United States Patent [19]

Tanaka et al.

[11] Patent Number: 4,961,341
[45] Date of Patent: Oct. 9, 1990

[54] TESTING DEVICE FOR AN OXYGEN SENSOR

[75] Inventors: Masashi Tanaka, Takatsuki; Shigekazu Yamauchi, Nagaokakyo; Masaru Mikita, Kyoto, all of Japan

[73] Assignee: Mitsubishi Jidosha Kogyo Kabushiki Kaisha, Tokyo, Japan

[21] Appl. No.: 356,440

[22] Filed: May 23, 1989

[30] Foreign Application Priority Data

May 31, 1988 [JP] Japan ................. 63-131754

[51] Int. Cl.⁵ .......................................... G01M 15/00
[52] U.S. Cl. .................................. 73/118.1; 73/865.6
[58] Field of Search ............... 73/118.1, 1 G, 865.6, 73/118.1; 436/137

[56] References Cited

U.S. PATENT DOCUMENTS 3,776,023 12/1973 Badd et al. ........................ 73/1 G
4,825,683 5/1989 Takami et al. .................... 73/1 G Primary Examiner—Jerry W. Myracle
Attorney, Agent, or Firm—Abelman Frayne Rezac & Schwab

[57] ABSTRACT

An oxygen sensor testing device having an oxygen sensor disposed in a rear stage of a synthetic gas passage to evaluate the oxygen sensor using a synthetic gas supplied to the synthetic gas passage, in which a sulfur dioxide gas passage supplied with sulfur dioxide gas communicates with a front stage of the synthetic gas passage to supply sulfur dioxide gas to the synthetic gas passage, thereby enabling exact evaluation of the oxygen sensor using the synthetic gas having composition close to actual exhaust gas containing sulfur dioxide.

13 Claims, 5 Drawing Sheets

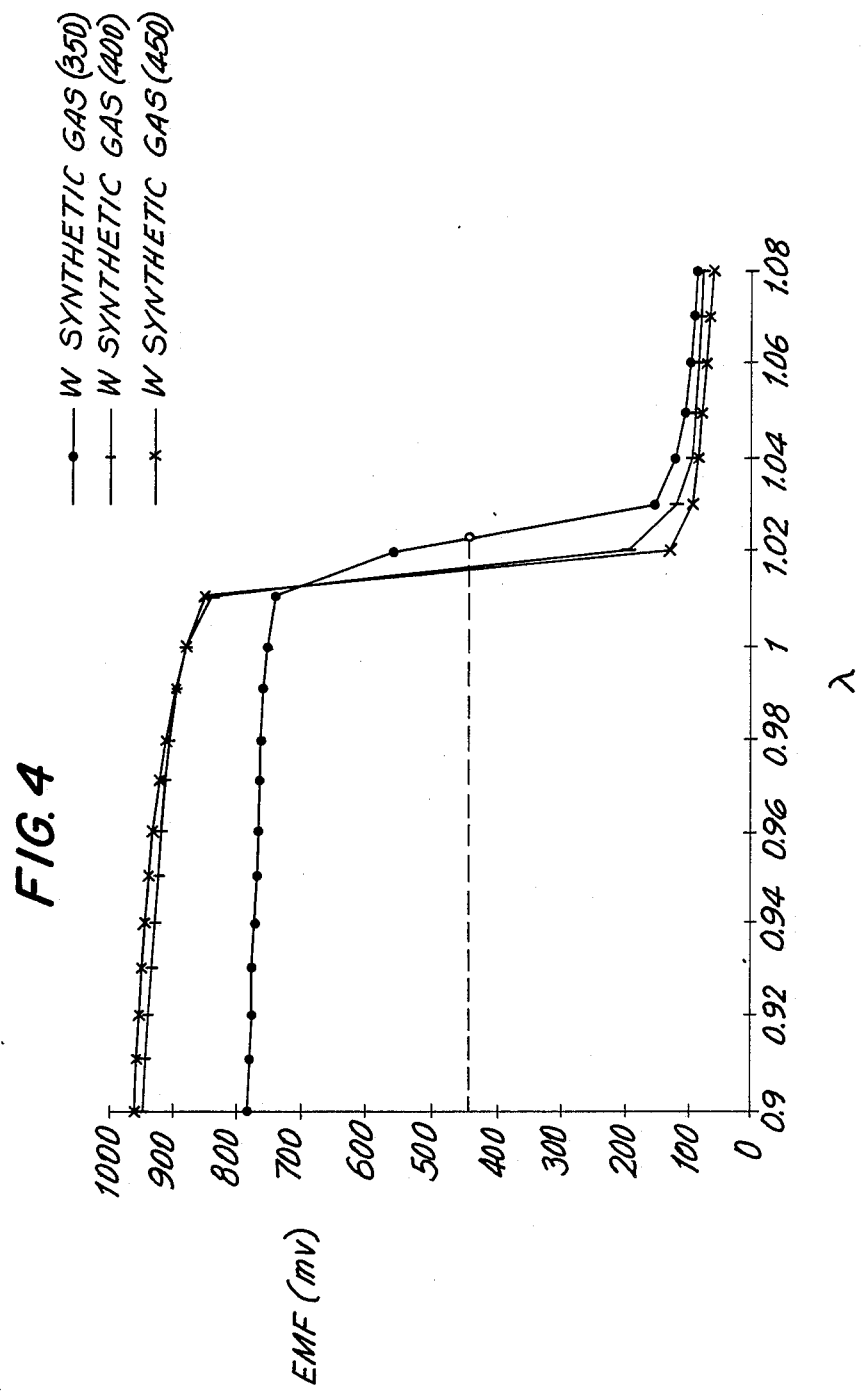

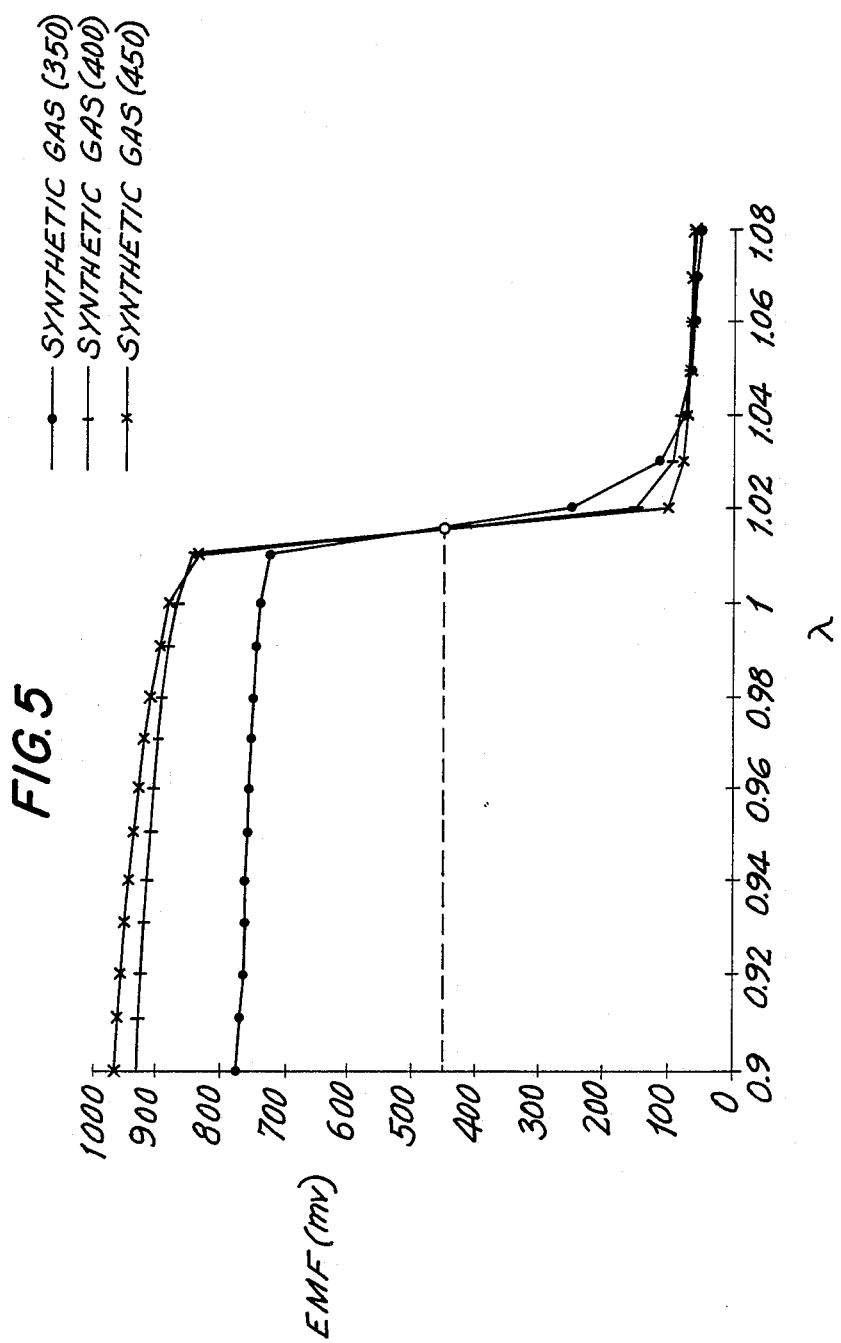

TESTING DEVICE FOR AN OXYGEN SENSOR

FIELD OF THE INVENTION

This invention relates to a testing device to test and evaluate the performance of an oxygen sensor used in an air/fuel ratio control or the like of an internal combustion engine for a vehicle.

BACKGROUND OF THE INVENTION

Ratio of air and fuel, or air/fuel ratio, of the air/fuel mixture supplied to an internal combustion engine is controlled in accordance with the operating conditions of the vehicle to suppress noxious substances in the exhaust gas and/or to enhance the thermal efficiency of the engine. This control is performed using an oxygen sensor ($O_2$ sensor) for detecting oxygen concentration of the exhaust gas and an air/fuel ratio control device for controlling the air/fuel ratio fo the air/fuel mixture. The oxygen sensor is employed to feedback control the air/fuel control device in dependence on the output of the $O_2$ sensor, so that the air/fuel ratio of the air/fuel mixture is near the stoichiometric mixture ratio. The $O_2$ sensor used in air/fuel ratio control is tested and evaluated for its output and response characteristics using a testing device.

Conventional testing devices include those which use combustion gas of a propane burner to test $O_2$ sensors, and those which use exhaust gas of an actual engine to test $O_2$ sensors. In the device using a propane burner, output and response characteristics of $O_2$ sensors are evaluated using the combustion gas. The device using an actual engine uses a computer to control the composition of air/fuel mixture to higher fuel concentrations than the stoichiometric mixture ratio (rich condition) or lower fuel concentrations than the stoichiometric mixture ratio (lean condition), and output and response characteristics of $O_2$ sensors are evaluated using exhaust gas close to that of actual vehicles under rich, lean, and transient conditions.

The $O_2$ sensor using a propane burner, since it is not able to evaluate exact characteristics because the composition of the combustion gas differs from that of actual exhaust gas, is used only for confirmation of quality control of $O_2$ sensors.

Evaluation of $O_2$ sensors using exhaust gas of an actual engine is expected to provide the same results as evaluation of exhaust gas of actual vehicles. However, the engine varies in characteristics as it is operated for an extended period of time, and, if the engine is replaced with another one, evaluation results may differ even for the same $O_2$ sensor, with poor test reliability. Furthermore, when the air/fuel ratio of mixture varies from rich to lean condition, or lean to rich condition, or when such variation occurs abruptly, conditions which are most important to evaluate the characteristics of $O_2$ sensors, the engine must be operated at a high speed and under a heavy load. This adversely affects the engine and impairs the reproducibility of the test. Therefore, evaluation of $O_2$ sensors has been reliable only when the engine is operated at a low speed and with a light load. Evaluation of characteristics of $O_2$ sensors has been inaccurate when the air/fuel ratio of mixture varies largely or abruptly.

With a view to obviating the above prior art defects, it is a primary object of the present invention to provide a testing device for oxygen sensors which is able to create an exhaust gas of composition close to that of actual exhaust gas and containing constituents adversely affecting evaluation of $O_2$ sensors, and, to simulate exhaust gas of various running conditions of the vehicle with good repeatability. This enables evaluation of $O_2$ sensors under conditions close to those of actual driving conditions, and improves reliability of the test.

SUMMARY OF THE INVENTION

In accordance with the present invention, an oxygen sensor is disposed in a rear stage of a synthetic gas passage to evaluate the oxygen sensor using a synthetic gas supplied to the synthetic gas passage. A sulfur dioxide gas passage supplied with sulfur dioxide gas communicates with a front stage of the synthetic gas passage, thereby evaluation of the oxygen sensor using the synthetic gas admixed with sulfur dioxide.

By controlling the composition of the admixture supplied to the synthetic gas passage, variation rate and variation condition of the gas composition can be flexibly selected to simulate changes in air/fuel ratio of rich or lean conditions with good reproducibility.

BRIEF DESCRIPTION OF THE DRAWINGS

FIG. 4 is a graph showing relation between electromotive force of an $O_2$ sensor and $O_2$ excess rate when using a synthetic gas containing $SO_2$.

FIG. 5 is a graph showing relation between electromotive force of an $O_2$ sensor and $O_2$ excess rate when using a synthetic gas not containing $SO_2$.

DESCRIPTION OF THE PREFERRED EMBODIMENT

Figure 1:
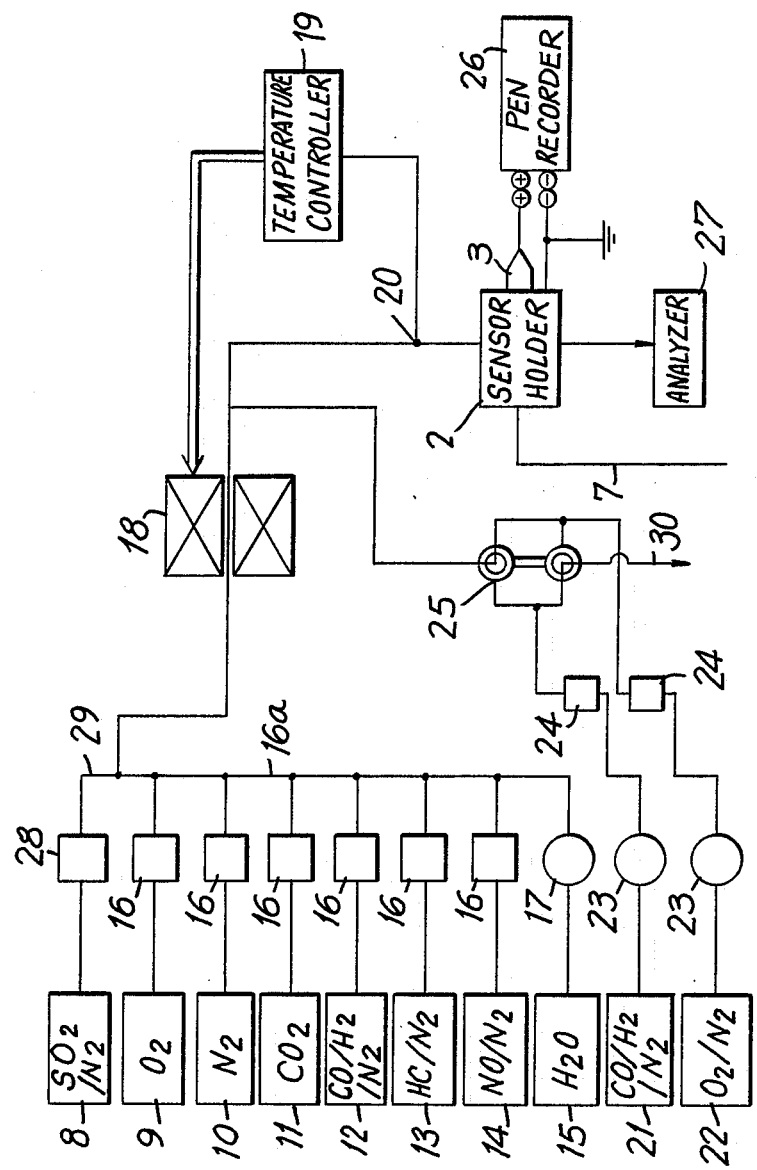
FIG. 1 is a schematic view showing an embodiment of the testing device according to the present invention.
Figure 2:
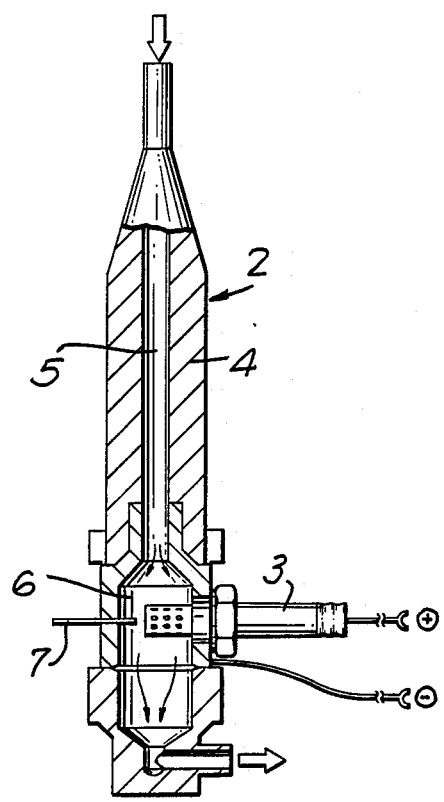
FIG. 2 is a schematic cross sectional view of a sensor holder.

FIG. 1 is a schematic view showing structure of an embodiment of the testing device according to the present invention, and FIG. 2 is a schematic cross sectional view of a sensor holder. A sensor holder 2 is disposed in a rear stage of a synthetic gas passage 1. The sensor holder 2 holds an $O_2$ sensor 3 which is tested using a synthetic gas supplied into the synthetic gas passage 1. As shown in FIG. 2, the sensor holder 2 is provided with a gas passage 5 in a high-temperature insulation layer 4, and the $O_2$ sensor 3 is held in a gas chamber 6 of the gas passage 5. The gas chamber 6 is provided with a thermocouple 7 to measure the gas temperature in the gas chamber 6.

A front stage of the synthetic gas passage 1 communicates with gas cylinders and tanks for gases comprising the synthetic gas. Specifically, a first cylinder 8 is filled with sulfur dioxide gas ($SO_2$) and nitrogen gas ($N_2$); a second cylinder 9 with oxygen gas ($O_2$); a third cylinder 10 with nitrogen gas ($N_2$); a fourth cylinder 11 with carbon dioxide gas ($CO_2$); a fifth cylinder 12 with carbon monoxide gas (CO), hydrogen gas ($H_2$) and nitrogen gas ($N_2$); a sixth cylinder 13 with a hydrocarbon gas (HC) and nitrogen gas ($N_2$); a seventh cylinder 14 with nitrous oxide gas (NO) and nitrogen gas ($N_2$); and, a tank 15 with water ($H_2O$). The first cylinder 8 communicates with the synthetic gas passage 1 through a flow metering device 28 and a sulfur dioxide passage 29. The second to seventh cylinders 9 to 14 communicate with the synthetic gas passage 1 through flow metering devices 16. The tank 15 communicates with the synthetic gas passage 1 through a pressure controller 17. Output of sensors (not shown) for detecting mass flow rates of gases passing through gas passages 29 and 16a in which the metering devices 16 and 28 are provided, make feedback control of gas flow rates so that mass flow rates of gases passing through the gas passages 29 and 16a are target values. The target value of sulfur dioxide is set to a value set on the basis of the sulfur content of a fuel for the internal combustion engine (e.g. 16 ppm for gasoline as a fuel, as described later in detail).

A middle stage of the synthetic gas passage 1 is provided by an electric furnace 18 as a heating device, which is ON/OFF controlled in response to a signal from a temperature controller 19. The synthetic gas passage 1 is provided in front of the sensor holder 2 with a thermocouple 20 as a temperature sensor, which is connected to the temperature controller 19. Thus, the temperature of the synthetic gas in front of the sensor holder 2 is measured by the thermocouple 20 and, according to the temperature measured, the electric furnace 18 is ON/OFF controlled through the temperature controller 19 to adjust the temperature of the synthetic gas with which the $O_2$ sensor 3 is tested.

In addition, an eighth cylinder 21 is filled with CO, $H_2$, and $N_2$, and a ninth cylinder 22 is filled with $O_2$ and $N_2$. The eighth cylinder 21 and the ninth cylinder 22 are respectively connected to a synchronous electromagnetic valve 25 through a pressure controller 23 and a flow meter 24. One outlet of the synchronous electromagnetic valve 25 communicates with the synthetic gas passage 1 at a position between the electric furance 18 and the sensor holder 2, specifically between the electric furnace 18 and the thermocouple 20, and the other outlet communicates with an open passage 30. Thus, by switching the synchronous electromagnetic valve 25, the gas in the eighth cylinder 21 and the gas in the ninth cylinder 22 are selectively fed into the synthetic gas passage 1 to selectively simulate exhaust gases of rich condition and lean condition. The ratio of the rich and lean conditions is controlled by the pressure controller 23 and the rate of change in rich and lean conditions is controlled by switching timing of the synchronous electromagnetic valve 25. Since the synchronous electromagnetic valve 25 is arranged to instantly switch the connection of the eighth cylinder 21 and the ninth cylinder 22 with the synthetic gas passage 1 and the open passage 30, the eighth cylinder 21 and the ninth cylinder 22 are always connected either to the synthetic gas passage 1 or the open passage 30. The flow rates of gases supplied from the cylinders 21 and 22 are almost constant, and a gas of the desired flow rate is introduced into the synthetic gas passage 1 even immediately after switching the synchronous electromagnetic valve 25.

In FIG. 1, numeral 26 indicates a pen recorder, and numeral 27 indicates an analyzer for analyzing the measurement results of the $O_2$ sensor 3. The pen recorder 26 and the analyzer 27 function as monitor devices for monitoring the output of the $O_2$ sensor 3.

In the above-described testing device, $SO_2$ in the first cylinder 8 is fed to the synthetic gas passage 1 through the sulfur dioxide gas passage 29, to add $SO_2$ to a gas from the second cylinder 9 to the ninth cylinder 14, and the synthetic gas containing $SO_2$. The temperature of the synthetic gas containing $SO_2$ is measured by the thermocouple 20, and operation of the electric funace 18 is controlled through the temperature controller 19 to adjust the temperature of the $SO_2$-containing synthetic gas at a specified value. The temperature-controlled $SO_2$-containing synthetic gas is introduced from the gas passage 5 to the gas chamber 6, where it diffuses and is detected by the $O_2$ sensor 3. The detection results are recorded by the pen recorder 26, the data is analyzed by the analyzer 27, and characteristics and response of the $O_2$ sensor 3 are evaluated.

To simulate exhaust gases of rich and lean air/fuel ratios, the synchronous electromagnetic valve 25 is switched to vary the composition of the $SO_2$-containing synthetic gas. The rate of change between the rich and lean conditions is controlled by varying the switching timing of the synchronous electromagnetic valve 25.

Since the above-described testing device for the $O_2$ sensor 3 uses the synthetic gas containing $SO_2$ which occurs in actual exhaust gases and affects evaluation of the $O_2$ sensor 3, conditions of exhaust gases close to those of actual vehicles can be simulated. Furthermore, by switching the synchronous electromagnetic valve 25, exhaust gases of air/fuel ratios of rich and lean conditions can be simulated, and the rate of change in rich and lean conditions can also be simulated easily and with good reproducibility. Use of such a gas introduction system including the synchronous electromagnetic valve 25 is particularly effective in the simulation of transient conditions such as speed up and down of the vehicle. This is because, with only a gas introduction system such as the flow controller 16 which makes feedback control to achieve exact flow control, sufficient transient response characteristic cannot be obtained, which may constitute a problem in reproducibility of conditions of actual vehicles. (Since the $SO_2$ content is not varied even in transient operation conditions, this embodiment does not use a special gas ($SO_2$) introduction system for transient response.)

Conditions in which $SO_2$ affects evaluation of the $O_2$ sensor 3 will be described with reference to the test results. A first test will now be described. Using an $SO_2$-containing synthetic gas (hereinafter referred to as W synthetic gas) and a synthetic gas without $SO_2$ (simply referred to as synthetic gas) and varying rich and lean conditions, relationship between the repetition period (half period) (sec) of variation in rich and lean conditions and the response time (Tr1: msec) of the $O_2$, sensor 3 was investigated.

The reason why the $SO_2$ content was set to 16 ppm will be described. It is assumed that when the air/fuel ratio is 14.7, that is air/fuel=14.7 g/1 g, 100 ppm of sulfur (S) is contained in 1 g of fuel (gasoline). Average S contents of fuel are 50–60 ppm in Japan, about 300 ppm in the US, and 300–400 ppm in West Germany and Australia.

Weight of S in fuel is $$S = 1 \times 100 \times 10^{-6} (g)$$

$$= 1 \times 10^{-4} (g)$$

When all of the S of $1 \times 10^{-4}$ (g) is converted to $SO_2$ and exhausted, (atomic weight of S: 32, molecular weight of $SO_2$: 64).

$1 \times 10^{-4}$ (g)/32 = $3.125 \times 10^{-6}$ mole of S is converted to $3.125 \times 10^{-6}$ mole of $SO_2$.

Applying the equation of PV=nRT, $3.125 \times 10^{-6}$ mole of $SO_2$ at 1 atm and 25° C. has a volume of $$1 \times V = 3.125 \times 10^{-6} \times 0.082 \times (273 + 25)$$

$$V = 7.63625 \times 10^{-5}(l)$$

With an average molecular weight of 28, 14.7 g of air at 1 atm and 25° C. has a volume of $$1 \times V = 14.7/28 \times 0.082 \times (273+25)$$

$$V = 12.8289(l)$$

Since 1 g of the fuel contains $1 \times 10^{-4}$ (g) of S, the remaining amount of the fuel is $1 - 1 \times 10^{-4} = 0.9999(g)$ which, with the average molecular weight assumed as 100, at 1 atm and 25° C., has a volume of $$1 \times V = 0.9999/100 \times 0.082 \times (273+25)$$

$$V = 0.24434(l)$$

Therefore, when the fuel contains 100 ppm of S, the $SO_2$ concentration of the exhaust gas is $$7.63625 \times 10^{-5}/(12.8289 + 0.24434) = 5.84 \times 10^{-6}$$

$$= 5.84(ppm)$$

When S is contained in larger amounts in the fuel as in West Germany, for example, 400 ppm, $SO_2$ concentration of exhaust gas is about 24 ppm. In view of fluctuations in S concentration of fuel and transient changes in $SO_2$ due to absorption and desorption by catalysts, when testing the $O_2$ sensor 3, it is preferable to set the $SO_2$ concentration to about 16 ppm. Thus, in comparative tests of the synthetic gas and W synthetic gas, the $SO_2$ concentration of the W synthetic gas is set to 16 ppm. It is desirable that the testing device can supply up to about 3-times the maximal $SO_2$ concentration (24 ppm in this embodiment), in order to accommodate various operation conditions and for effective testing procedures.

Figure 3:
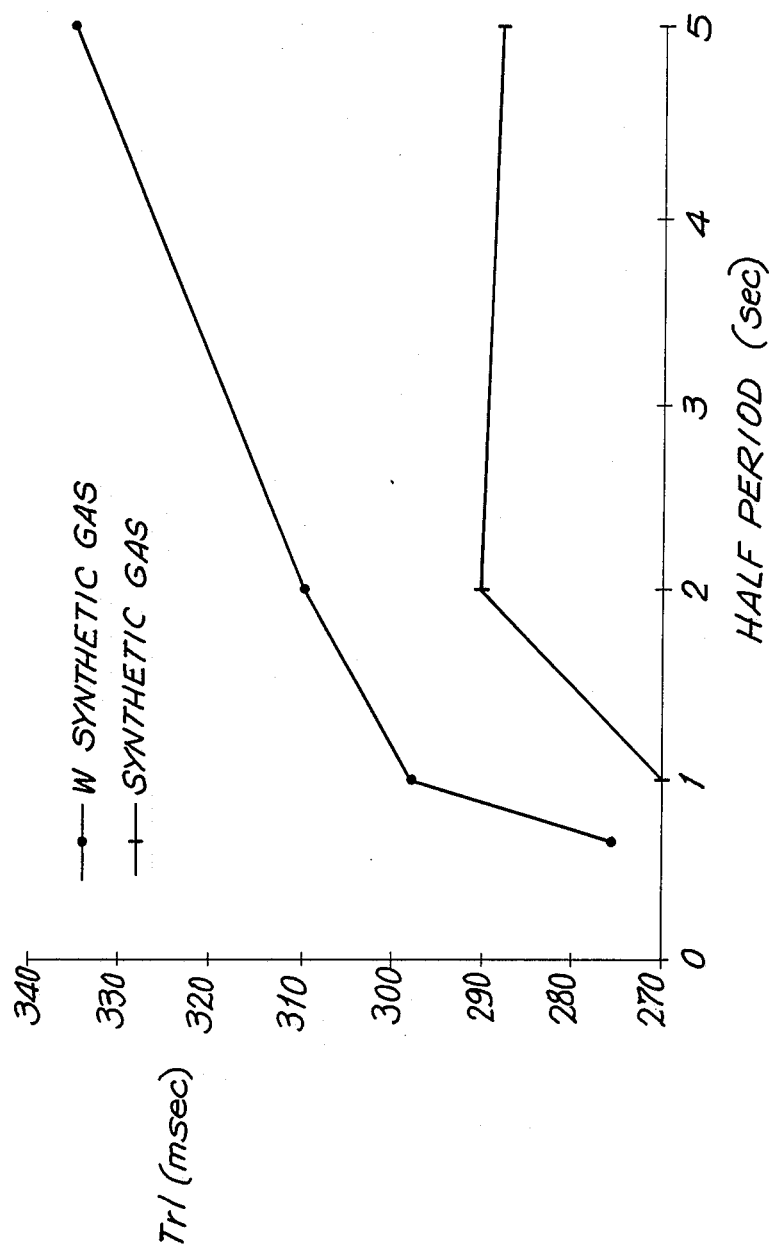
FIG. 3 is a graph showing relation between synthetic gas composition and response of an $O_2$ sensor.

Tests were carried out using the W synthetic gas and the synthetic gas to check the response time of the $O_2$ sensor 3 to repetitions of change in rich and lean conditions, with different repetition periods. The results are shown in FIG. 3. The graph shown in FIG. 3, with the response time on the ordinate and the repetition period of rich and lean conditions on the abscissa, shows relationship between the gas composition and response.

When the W synthetic gas is used, the response time of the $O_2$ sensor 3 increases with increasing repetition period of change in rich and lean conditions. With the synthetic gas used, the response time of the $O_2$ sensor 3 increases with increasing repetition period of change in rich and lean conditions up to 2 sec but, for longer repetition periods than 2 sec, the response time of the $O_2$ sensor 3 is constant. With the synthetic gas, no changes in the response time of the $O_2$ sensor 3 occur when the repetition period of change in rich and lean conditions exceeds 2 sec. When the W synthetic gas is used, the response time of the $O_2$ sensor 3 tends to increase as the repetition period of change in rich and lean conditions increases. Therefore, different results are obtained between the cases when $SO_2$ is contained in the synthetic gas and is not. Thus, as in the testing device shown in FIg. 1, by performing the test of the $O_2$ sensor 3 using the synthetic gas containing $SO_2$ which is contained in actual exhaust gases (W synthetic gas), the sensor can be tested under conditions close to actual exhaust gases, thereby obtaining reliable evaluation results.

A second test will now be described. This test uses the W synthetic gas and the synthetic gas, which are heated to 350° C., 400° C., and 450° C. Using the W synthetic gas and the synthetic gas, relationship between $O_2$ excess rate ($\lambda$) and electromotive force (EMF: mV) of the $O_2$ sensor 3 was investigated. The $O_2$ excess rate $\lambda$ is ratio of the actual air/fuel ratio and the theoretical air/fuel ratio $\lambda =$ (actual air/fuel ratio)/(theoretical air/fuel ratio) and when $\lambda = 1$, air/fuel ratio is 14.6 to 14.7.

The results are shown in FIG. 4 and FIG. 5. The graphs shown in FIG. 4 and FIG. 5, with the electromotive force: EMF of the $O_2$ 3 on the ordinate and the $O_2$ excess rate: $\lambda$ on the abscissa, show the $\lambda$-EMF characteristics. When the W synthetic gas is used, heated to 400° C. and 450° C., respectively (W synthetic gas (400), W synthetic gas (450)), $\lambda$ is about 0.9 to 1.01 with an EMF of 900 mV to 950 mV; when $\lambda$ is about 1.02, EMF rapidly decreases to 150 mV to 200 mV, and when $\lambda$ is over 1.02, EMF is almost constant at abut 100 mV. When the W synthetic gas heated to 350° C. (W synthetic gas (350)) is used, $\lambda$ is about 0.9 to 1.01 with an EMF of about 780 mV. When $\lambda$ is about 1.02, EMF drops to 550 mV, and when $\lambda$ is about 1.03, EMF drops to about 150 mV. For $\lambda$ of over 1.03, EMF is almost constant. When the synthetic gas, heated to 400° C. and 450° C., respectively (synthetic gas (400), synthetic gas (450)), almost the same results are obtained as with the W synthetic gas (400) and the W synthetic gas (450). When the synthetic gas heated to 350° D. (synthetic gas (350)) is used, $\lambda$ is 0.9 to 1.01 with an EMF of about 780 mV. When $\lambda$ is about 1.02, EMF sharply decreases to 150 mV, and when $\lambda$ is over 1.03, EMF is almost constant. It can be seen that, at 400° C. and 450° C., there are no substantial differences in $\lambda$-EMF characteristics between the synthetic gas and the W synthetic gas, however, at 350° C., the synthetic gas containing $SO_2$ shows different characteristics. Normally, the $O_2$ sensor 3 determines the rich and lean conditions with an EMF of 450 mV. Comparing FIG. 4 and FIG. 5, the W synthetic gas (350) affords a 450 mV EMF with $\lambda$ of about 1.025, while the synthetic gas (350) affords an 450 mV EMF with $\lambda$ of about 1.017, thus showing a dfference. Therefore, since at a temperature of 350° C., there occur differences in characteristics between the synthetic gas without $SO_2$ which is contained in actual exhaust gas and the synthetic gas containing $SO_2$ (W synthetic gas), reliable evaluation results can be obtained by testing the $O_2$ sensor 3 using the synthetic gas containing $SO_2$ which is contained in actual exhaust gas, representing the conditions close to those of actual exhaust gas, as with the testing device shown in FIG. 1.

As obvious from the above two tests results, when testing the $O_2$ sensor 3, output and response characteristics of the $O_2$ sensor 3 vary with conditions whether or not the synthetic gas contains $SO_2$ which is contained in actual exhaust gas. Therefore, as in the testing device shown in FIG. 1, output and response characteristics can be obtained by testing the $O_2$ sensor 3 using the $SO_2$-containing synthetic gas under conditions very close to those of actual exhaust gas, thereby enabling reliable evaluation.

The above-described testing device for the $O_2$ sensor 3, which tests the $O_2$ sensor 3 using the synthetic gas containing $SO_2$, can test the characteristics and performance of the $O_2$ sensor 3 using the synthetic gas simulating the conditions close to actual exhaust gas. The device is capable of varying $\lambda$ in a wide range ($\pm 0.1$) to simulate rich and lean conditions and transient conditions of exhaust gas, with stable composition of the synthetic gas and with good accuracy and reproducibility, and is thus useful in the elucidation of deterioration mechanism. Furthermore, since gases from the cylinders 21 and 22 which are not passed through the electric furnace 18 are introduced to the synthetic gas passage 1 at the upstream of the thermocouple 20, temperature of the synthetic gas introduced into the $O_2$ sensor 3 is controlled very exactly.

In the oxygen sensor testing device according to the present invention, since the sulfur dioxide gas passage to supply $SO_2$ communicates with the synthetic gas passage, the synthetic gas is obtained which has close composition to actual exhaust gas containing sulfur dioxide, which affects evaluation oxygen sensors, and the synthetic gas containing $SO_2$ can be simulated to conditions of exhaust gas under various running conditions with good reproducibility. As a result, evaluation of oxygen sensors is possible using the synthetic gas having a composition close to actual exhaust gas containing $SO_2$ under rich and lean air/fuel ratios and transient conditions, thereby enabling exact and reliable evaluation of the oxygen sensor.

We claim:

1. An oxygen sensor testing device comprising:
a plurality of gas supply sources individually storing various specific gas constituents of exhaust gas of an internal combustion engine;
means providing a gas passage supplied with said various specific gas constituents from said plurality of gas supply sources and capable of forming a synthetic gas corresponding to internal combustion engine exhaust gas;
an oxygen sensor connected to said synthetic gas passage and supplied with said synthetic gas from said synthetic gas passage;
a monitoring device for monitoring an output of said oxygen sensor; and,
individual metering devices disposed in individual connection passages connecting said individual gas supply sources and said synthetic gas passage;
one of said plurality of gas supply sources being a sulfur dioxide supply source to supply said synthetic gas and sulfur dioxide, and said synthetic gas being introduced into said oxygen sensor to test and evaluate said oxygen sensor.

2. The oxygen sensor testing device as claimed in claim 1, wherein said gas supply sources include at least an oxygen supply source storing oxygen and a carbon dioxide supply source storing carbon dioxide and a carbon monoxide supply source storing carbon monoxide, and said specific gas constituents and said sulfur dioxide are metered by said individual metering devices.

3. The oxygen sensor testing device as claimed in claim 2, wherein a flow rate of sulfur dioxide supplied from said sulfur dioxide supply source is adjusted by a flow controller so that a content of sulfur dioxide of said synthetic gas is a value set according to a content of sulfur dioxide of fuel of said internal combustion engine.

4. The oxygen sensor testing device as claimed in claim 2, wherein said sulfur dioxide supply source is a gas vessel charged with a mixture of sulfur oxide and nitrogen.

5. The oxygen sensor testing device as claimed in claim 2, wherein said individual metering devices operate to bring actual flow rates of said specific gas constituent passages closer to target flow rates in dependence on results of comparison of said actual flow rates with said target flow rates, and said synthetic gas passage communicates with a transient testing gas passage conducting at least one of oxygen and carbon monoxide independently of said connection passages.

6. The oxygen sensor testing device as claimed in claim 2, further comprising a heating unit for heating said synthetic gas disposed in said synthetic gas passage.

7. The oxygen sensor testing device as claimed in claim 6, further comprising a temperature sensor for detecting the temperature of said synthetic gas disposed in said synthetic gas passage between said heating unit and said oxygen sensor and a control device for outputting a control signal in response to the output of said temperature sensor to said heating unit to adjust the temperature of said synthetic gas to a target value.

8. The oxygen sensor testing device as claimed in claim 6, wherein said synthetic gas passage between said heating unit and said oxygen sensor communicates with a transient testing gas passage conducting at least one of oxygen and carbon monoxide.

9. The oxygen sensor testing device as claimed in claim 8, further comprising a temperature sensor for detecting temperature of said synthetic gas disposed in said synthetic gas passage between the communication position of said transient testing gas passage and said oxygen sensor and a control device for outputting a control signal in response to the output of said temperature sensor to said heating unit to adjust the temperature of said synthetic gas to a target value.

10. The oxygen sensor testing device as claimed in claim 8, wherein said transient testing gas passage is provided with an oxygen supply passage for conducting oxygen and a carbon monoxide supplying passage conducting carbon monoxide and a valve mechanism for providing exclusive communication of one of said oxygen and carbon monoxide supply passages with said synthetic gas passage.

11. The oxygen sensor testing device as claimed in claim 1, wherein said synthetic gas passage communicates with a transient testing gas passage connected with both an oxygen supply source and a carbon monoxide supply source, and said transient testing gas passage is provided with an oxygen supply passage connected with said oxygen supply source and a carbon monoxide supply passage connected with said carbon monoxide supply and a valve mechanism for providing exclusive communication of one of said oxygen and carbon monoxide supply passages with said synthetic gas passage.

12. The oxygen sensor testing device as claimed in claim 11, wherein said valve mechanism is arranged so that when one of said oxygen and carbon monoxide supply passages is connected with said synthetic gas passage, the other of said oxygen and carbon monoxide supply passages communicates with an open passage, and connection condition of said oxygen and carbon monoxide passages with said synthetic gas passage and said open passage can be switched instantly.

13. The oxygen sensor testing device as claimed in claim 11, wherein said valve mechanism performs cyclic switching operation of said oxygen and carbon monoxide passages.

* * * * *